(12) United States Patent
Korten et al.

(10) Patent No.: US 10,245,126 B2
(45) Date of Patent: Apr. 2, 2019

(54) METHOD OF MAKING A DENTAL RESTORATION BY MATCHING TOOTH COLOR STRUCTURE FROM AN IMAGE OF A TOOTH WITH BLOCK COLOR STRUCTURE OF A RESTORATIVE MATERIAL

(71) Applicant: 3M INNOVATIVE PROPERTIES COMPANY, St. Paul, MN (US)

(72) Inventors: Malte Korten, Moorenweis (DE); Helmar B. Mayr, Kaufering (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 22 days.

(21) Appl. No.: 15/515,238

(22) PCT Filed: Oct. 16, 2015

(86) PCT No.: PCT/US2015/055887
§ 371 (c)(1),
(2) Date: Mar. 29, 2017

(87) PCT Pub. No.: WO2016/073162
PCT Pub. Date: May 12, 2016

(65) Prior Publication Data
US 2017/0231731 A1    Aug. 17, 2017

(30) Foreign Application Priority Data
Nov. 7, 2014 (EP) ................................. 14192264

(51) Int. Cl.
*A61C 13/00* (2006.01)
*A61C 13/08* (2006.01)
(Continued)

(52) U.S. Cl.
CPC .............. *A61C 13/082* (2013.01); *A61B 1/24* (2013.01); *A61C 13/0004* (2013.01);
(Continued)

(58) Field of Classification Search
CPC . A61C 13/09; A61C 13/0004; A61C 13/0022; A61C 13/082; A61C 19/10;
(Continued)

(56) References Cited

U.S. PATENT DOCUMENTS 5,800,164 A * 9/1998 Pfau .................. A61C 13/082
433/203.1
6,007,332 A * 12/1999 O'Brien ................ A61C 19/10
356/404

(Continued)

FOREIGN PATENT DOCUMENTS

| CN | 102254317 | 11/2011 |
|---|---|---|
| DE | 202008014344 | 3/2010 |

(Continued)

OTHER PUBLICATIONS

International Search Report for PCT International Application No. PCT/US2015/055887, dated Jan. 29, 2016, 5 pages.

*Primary Examiner* — Chun Cao (57) ABSTRACT

A method of making a dental restoration has the steps of capturing an image of a tooth, posterizing the image, determining a tooth color structure, providing information about a multicolored block having a block color structure, matching the tooth color structure and the block color structure, based on the matching, determining a position within the block in which the tooth color structure and the block color structure match, and machining the dental restoration from the block at the determined position. The invention helps facilitating the making of dental restorations at maximized aesthetics.

14 Claims, 4 Drawing Sheets

(51) Int. Cl.

| | | |
|---|---|---|
| *A61C 13/09* | (2006.01) | |
| *G01J 3/50* | (2006.01) | |
| *G06T 7/12* | (2017.01) | |
| *G06T 7/90* | (2017.01) | |
| *A61B 1/24* | (2006.01) | |
| *G01J 3/46* | (2006.01) | |
| *G06T 7/00* | (2017.01) | |
| *A61C 19/10* | (2006.01) | |

(52) U.S. Cl.
CPC .......... *A61C 13/0022* (2013.01); *A61C 13/09* (2013.01); *G01J 3/463* (2013.01); *G01J 3/508* (2013.01); *G06T 7/0014* (2013.01); *G06T 7/12* (2017.01); *G06T 7/90* (2017.01); *A61C 19/10* (2013.01); *G06T 2207/30036* (2013.01)

(58) Field of Classification Search
CPC ......... G06T 2207/30036; G06T 7/0014; G06T 7/12; G06T 7/90; G06T 7/0083; G06T 7/408
USPC .................. 700/97, 98; 433/26, 202.1, 203.1
See application file for complete search history.

(56) References Cited

U.S. PATENT DOCUMENTS

| | | | | |
|---|---|---|---|---|
| 6,030,209 | A * | 2/2000 | Panzera | A61C 13/082 433/203.1 |
| 7,698,068 | B2 * | 4/2010 | Babayoff | A61B 1/00009 702/19 |
| 8,571,281 | B2 * | 10/2013 | Wong | G01J 3/46 382/128 |
| 10,010,387 | B2 * | 7/2018 | Esbech | G01J 3/504 |
| 2006/0177792 | A1 | 8/2006 | Touchstone | |
| 2011/0085713 | A1 | 4/2011 | Yan et al. | |
| 2014/0080095 | A1 * | 3/2014 | Suttin | A61C 13/34 433/202.1 |
| 2015/0289954 | A1 * | 10/2015 | Chang | A61C 13/0006 433/29 |

FOREIGN PATENT DOCUMENTS

| | | |
|---|---|---|
| EP | 1434164 | 6/2004 |
| WO | WO 2013/072287 | 5/2013 |
| WO | WO 2015/073365 | 5/2015 |

* cited by examiner

METHOD OF MAKING A DENTAL RESTORATION BY MATCHING TOOTH COLOR STRUCTURE FROM AN IMAGE OF A TOOTH WITH BLOCK COLOR STRUCTURE OF A RESTORATIVE MATERIAL

CROSS REFERENCE TO RELATED APPLICATIONS

This application is a national stage filing under 35 U.S.C. 371 of PCT/US2015/055887, filed Oct. 16, 2015, which claims priority to European Application No. 14192264.1, filed Nov. 7, 2014, the disclosures of which are incorporated by reference in their entireties herein.

FIELD OF THE INVENTION

The invention relates to a method of making a dental restoration, and in particular to a method in which a color structure of a tooth and an overall tooth color are independently determined. Based on such determination a dental restoration is machined from a multicolored block.

BACKGROUND ART

Dental restorations are often manufactured by an automated process, which typically includes:
- capturing the shape of a patient's teeth, for example by scanning a plaster model of the patient's teeth or alternatively by scanning the actual teeth in the patient's mouth;
- designing the shape of a dental restoration precursor based on the captured shape using a computer-aided design (CAD) software; and
- machining the dental restoration precursor to correspond to the designed shape, for example, by an automated Computer Numerical Controlled (CNC) machine.

It is desirable that the dental restoration has an appearance that matches or approximates the appearance of adjacent teeth. The appearance of natural teeth is on the one hand provided by color shades, and further by a certain translucency. A dental technician or a dental practitioner, for example, typically selects the color of the ceramic material to be used for the dental restoration according to the teeth in a patient's mouth that are located next to the tooth or teeth to be restored. For example, the appearance of relevant teeth in a patient's mouth may be determined using shade guides and an appropriate color shade for the framework and the veneer may be selected accordingly. Exemplary shade guide types are available under the designations "VITA Classical Shade Guide" or "VITA Toothguide 3D-Master®" from the company VITA Zahnfabrik H. Rauter GmbH & Co. KG, Germany. General types of materials for dental restorations are typically selected to meet certain mechanical and aesthetic requirements, which are for example the desired color and/or translucency.

Manufacturers of dental materials often offer dental restorative materials in a variety of different color shades, and a dental technician or a dental practitioner usually selects the shade of the material that is closest to the desired shade. Many approaches have been tried to provide dental restorative materials in color shades that match the desired color as closely as possible. There are also dental restorative materials in the form of milling or grinding blocks, which exhibit a certain pre-determined color gradation to approximate the appearance of the finished dental toward the appearance of a natural tooth.

Although the current approaches for manufacturing of dental restorations may provide a variety of advantages, there is still a desire for a method of manufacturing dental restorations in a reproducible, cost efficient manner and at a good aesthetic quality.

SUMMARY OF THE INVENTION

The invention in one aspect relates generally to a two-phase approach of determining a shade structure of a dental restoration. In one phase the overall color of a tooth, for example in a patient's mouth, is determined. In an independent or separate further phase the color structure, in particular the structure or proportioning of different color areas, of that tooth is determined.

In a particular aspect the invention relates to a method of making a dental restoration, which method comprises the steps of:
- capturing an image of a tooth at a color depth that is based on a multiplicity of color values;
- posterizing the image by:
  - detecting in the tooth image a contiguous first tooth color area having color values within a predetermined first range of different color values and assigning the first tooth color area one common first false color value;
  - detecting in the tooth image a contiguous second tooth color area having color values within a predetermined second range of different color values and assigning the second tooth color area one common second false color value;
- determining a tooth color structure based on the first and second false color value of the first and second color area, respectively, within the tooth image;
- providing information about a multicolored block that has a predetermined color shading formed by at least a first block color zone and a second block color zone, wherein the information comprises data about a block color structure with respect to dimensions and/or positions of the first and second block color zone;
- matching the tooth color structure and the block color structure; and based on the matching;
- determining a position within the block in which the tooth color structure and the block color structure match within predetermined limits; and
- machining the dental restoration from the block at the determined position.

The invention is advantageous in that it allows for the determination of a tooth color structure independent from the determination of the overall tooth color itself, and thus allows for maximizing the aesthetic appearance of a dental restoration. Further the selection of a block based simply on a tooth color code helps minimizing efforts and maximizing the accuracy of the color of the dental restoration. Nevertheless due to the multicolor structure of the block the inventions allows for providing the dental restoration with a color shading resembling that of a natural tooth.

The image is preferably captured digitally, for example using a digital camera or an intra-oral scanner. For the purpose of the present invention the term "image" as used herein refers to the optical image as well as the digital data representing the optical image. The step of capturing the tooth image may for example comprise taking a two-dimensional photograph from the tooth. Accordingly the image is preferably a two-dimensional representation of the tooth and for example provided in the form of a bitmap. Desirably the image is taken as a color image, for example at a color depth of about 16 million colors or more which is sometimes referred to as True Color Image in the art of computer graphics.

In an embodiment the step of capturing the tooth image may further comprise determining an outline of the tooth based on the two-dimensional photograph and thereby creating the tooth image. The outline may be determined manually or automatically. A computer may for example display the image taken and a user may define the tooth outline manually, for example by drawing a virtual line into the image. The computer may, based on this, assume the area of the image inside the outline as the tooth image. An automatic approach may be based for example on computer algorithms for edge finding.

For posterization of the image, in particular the data representing the image, the image may be converted into a grayscale image. The conversion from a color image into a grayscale image is well known in the art of computer graphics and implemented in many standard software packages for image processing. The conversion may be part of the detection of the contiguous first and second tooth color area. This is because the conversion of the color image of a great color depth into a grayscale image of fewer levels of gray also results in a partial posterization, because similar but different colors are assigned one common gray value. For the purpose of the present invention preferably the grayscale image is based on 256 levels (0-255) of gray. In a so formed grayscale image the first range of different color values may be defined between two threshold values within the grayscale, and that first range may be assigned a single color while the remainder of the grayscale forms the second range of different colors and is assigned a different single color. In one example the first false color value corresponds to white and the second false color value corresponds to black. It is noted that for the purpose of the present invention "black", "white" and "gray" are designated as "colors" although in other fields achromatic tones, like black, white and gray, may not be regarded as colors. This procedure which is based on the definition of thresholds is also referred to as "thresholding" in the art of computer graphics.

Accordingly in one embodiment the step of posterization is based on thresholding. The first false color value and the second false color value may particularly each correspond to a value in a grey scale or correspond to black and white, respectively. The skilled person will recognize that any color may be the basis for the first and second false color value as long as the first and second false color value are different. Further the skilled person will recognize other posterization procedures, for example procedures that are based on multiple different false color values.

In an embodiment the steps of capturing the image and posterizing may be performed in one common step, for example using appropriate hardware like a CCD camera operating based on more than the conventional three color filters.

The tooth color structure is preferably determined based on the first false color value and the second false color value in that the dimensions and positions of the first and second false colors are analyzed. This can be performed by a computer algorithm which analyzes the dimensions of any contiguous areas of the image being assigned a certain false color value, and the position of transitions between areas being assigned different false color values.

In a further embodiment the method further comprises the steps of:

providing a database holding information about a plurality of blocks with each of the blocks having a shade structure in accordance with the first and second block color zone, wherein each block being assigned an overall block color code which is based on the colors of the first and second block color zone in combination;

determining a tooth color code; and selecting a block having a block color code corresponding to the tooth color code.

The data about the block color structure may comprise (preferably three-dimensional) dimensions of the first and second block color zone. Further the data about the block color structure may comprise positions of the first and second block color zone relative to each other and relative to the outer boundaries of the block. The positions may be defined by coordinates in a three-dimensional coordinate system and optionally by orientations in that coordinate system. Further the position within the block in which the tooth color structure and the block color structure match may be defined by coordinates in a three-dimensional coordinate system and optionally by orientations in that coordinate system.

The method may further comprise the step of determining an average color value from the tooth image and calculating the tooth color code. In this embodiment the image taken for determining the tooth color structure may be used also for determining the tooth color and corresponding color code. In this regard the tooth color code preferably is a numerical or alphanumerical designation for a certain actual color. A common code system is for example defined in the VITA Shade System of the company VITA Zahnfabrik H. Rauter GmbH & Co. KG, Germany.

The method may further comprise the step of determining the tooth color code by matching a physical shade guide and the tooth. In this case the color and thus the color code are determined manually, for example by use of a shade guide or a color measuring device, both available from the company VITA Zahnfabrik H. Rauter GmbH & Co. KG, Germany. Automatic tooth color determination based on the image as described above and manual tooth color determination may be combined to maximize the accuracy in color determination.

In a further embodiment the method further comprises the steps of:

displaying at least part of the tooth image and the tooth color structure; and modifying boundaries of the tooth color structure based on user input.

This allows, for example, a manual modification of any automatically (by posterization or thresholding) determined color structure.

In an embodiment the method further comprises the steps of:

providing a three-dimensional virtual model of the dental restoration; and creating a positional relationship between the tooth color structure and the dental restoration model; and wherein the step of machining the dental restoration is controlled based on the dental restoration model.

For creating the positional relationship between the tooth color structure and the dental restoration model a two-dimensional view on the three-dimensional dental restoration model and the tooth color structure may be overlaid in the appropriate scale. The two-dimensional view may for example correspond to a view approximately perpendicular on the labial side of the tooth represented by the model, which essentially corresponds to the view from which the image is taken.

In a further embodiment, the method further comprises the steps of:
scanning a patient's teeth;
designing the dental restoration based on the scan and thereby providing the dental restoration model; and
transferring the dental restoration model by data transfer to a machine for machining the dental restoration.

The block may be made of a ceramic or glass ceramic material. Further the step of machining the dental restoration preferably involves milling and/or grinding. The dental restoration is preferably machined at a position in which the tooth color structure and the block color structure match. Such position may be determined based on the tooth color code, for example obtained by calculation or provided on a physical shade guide. The tooth color code may be input into a machine for machining the dental restoration manually or by electric data transfer. The machine may further be provided with the block color code of a block to be machined and may be configured (for example by software) for determining the position within the block at which the dental restoration is to be machined.

DETAILED DESCRIPTION OF THE INVENTION

Figure 1:
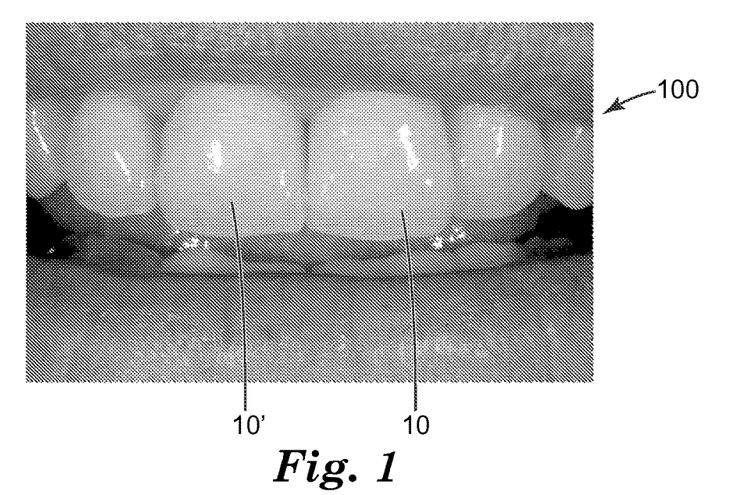
FIG. 1 is a view of a patient's teeth taken as image for use in the method according to an embodiment of the invention.

FIG. 1 illustrates an exemplary clinical situation 100 of some of a patient's teeth. The Figure shows a number of incisal teeth including a tooth 10 which for the sake of explanation of the invention is assumed to be a tooth to be restored. In the example the tooth to be restored 10 is present and in a condition to be used as reference for determining the desired shade structure and the desired color of a dental restoration intended to replace the tooth to be restored 10 or part of it. However, in other examples the tooth to be restored may not be present entirely or partly or may be present in a bad condition (for example stained or discolored) so that the determination of the desired shade structure and color of a dental restoration cannot be appropriately performed using the tooth to be restored as reference. In such a case a neighboring tooth 10' may be used as reference instead. In the following it is not consistently differentiated whether the tooth to be restored or any neighboring tooth is used as reference. The skilled person will understand that a suitable tooth can be selected as reference depending on the specific clinical situation of an individual patient. Further for the purpose of the present invention a "neighboring tooth" is not limited to mean any directly neighboring tooth but encompasses for example an opposite or another tooth adjacent the directly neighboring or opposite tooth.

According to one step of the method of the invention an image is captured of the clinical situation 100. The image taken from the clinical situation 100 comprises also partial images of individual teeth, such as the tooth to be restored 10 and the neighboring tooth 10'. In the example the image is taken in the form of a digital photograph using a camera. Typically the captured image is provided in the form of image data, for example a bitmap, having a certain color depth that is based on a multiplicity of color values. There are certain standard color depths available to the skilled person, like for example 256, 65536 or more different colors per image. At present photographs are typically taken at "True Color" which currently corresponds to a color depth of about 16 million different colors.

Figure 2:
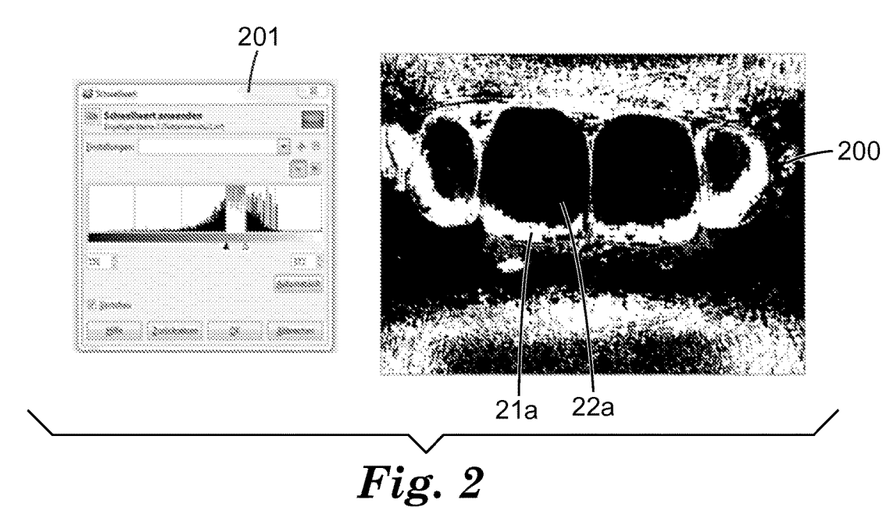
FIGS. 2, 3 illustrate the step of posterization according to an embodiment of the invention.

FIG. 2 illustrates a further step of the method of the invention. The image data provided by the camera are stored in a computer and are posterized. In the example the posterized image 200 is displayed, for example on a computer screen, to make it visible to a user. However in another example the posterization may be performed partly or entirely virtually without displaying. For posterization typically a color gradation based on a first color depth is converted to several single-colored regions based on a lower color depth, with abrupt changes between the different color regions to another. In the example contiguous color areas are determined in which the color values are within a predetermined range of different color values. Such areas are then assigned one common false color value. In particular in this example the color data of the image are virtually converted in grayscale data, using commonly known techniques. Based on this, areas of the image which correspond to a grayscale value within a range defined between a lower and upper threshold (in the example between 151 and 172 as shown in dialog box 201) are assigned a white color value and areas which correspond to a grayscale value outside that range are assigned a black color value. This allows for identifying one or more areas of a similar color or grayscale in the image and masking or fading out the remainder of the image. This step of the invention may be repeated based on a different range as shown in FIG. 3.

Figure 3:
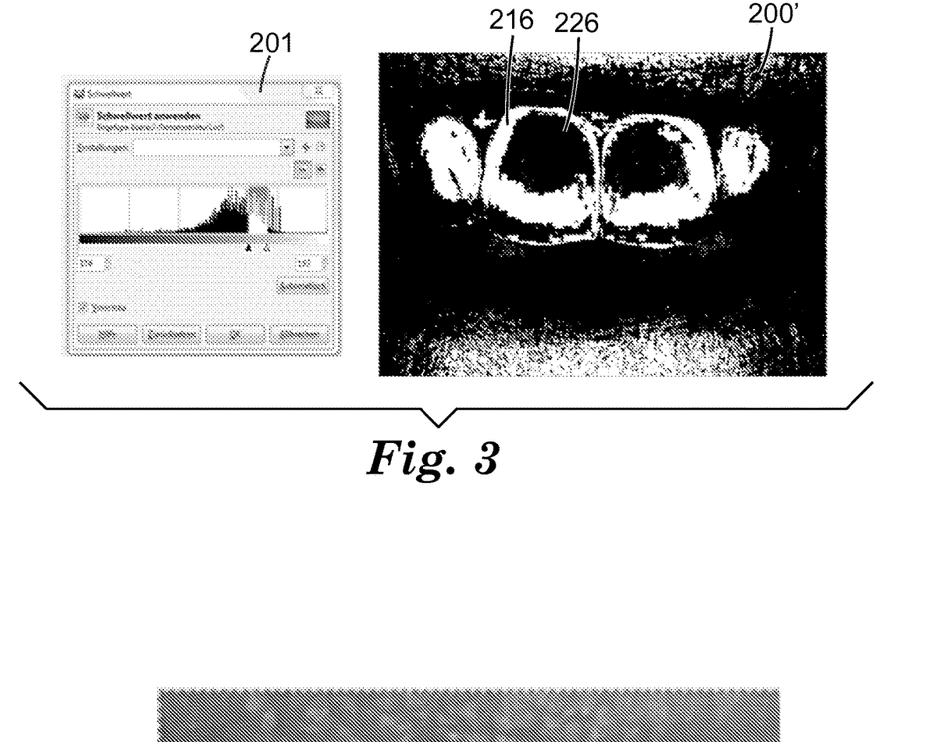

FIG. 3 shows a repetition of the step as described in FIG. 2, but with the threshold range selected differently. In this example the lower threshold is 174 and the upper threshold is 193 as shown as shown in dialog box 201. The posterized image 200' is different from the posterized image 200 in FIG. 2 in that it displays different contiguous areas of similar color.

In summary FIGS. 2 and 3 illustrate the detection of a contiguous first tooth color area (21a, 21b), which has color values within a predetermined first range of different color values. This first tooth color area (21a, 21b) is then assigned one common first false color value which in the example corresponds to white. Further FIGS. 2 and 3 illustrate the detection of a contiguous second tooth color area (22a, 22b) that has color values within a predetermined second range of different color values. The second tooth color area (22a, 22b) is assigned one common second false color value which in the example corresponds to black. The predetermined second range of different color values in the example corresponds to a composition of partial ranges outside the predetermined first range of different color values. For example in FIG. 2 the second range of different color values includes partial ranges 0-150 and 173-255, and in FIG. 3 the second range of different color values includes partial ranges 0-173 and 194-255.

Figure 4:
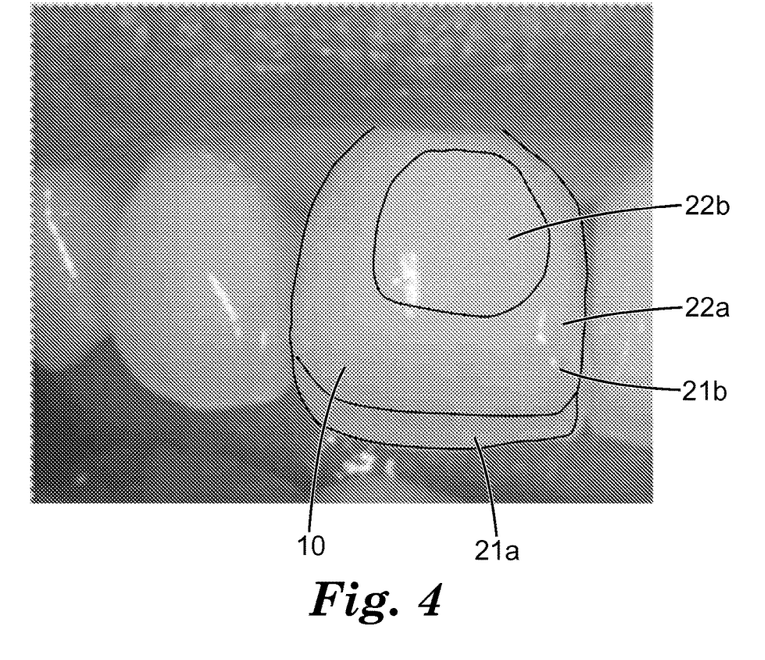
FIG. 4 visualizes boundaries of a tooth color structure as determined in a step of the method according to an embodiment of the invention.

The posterized image is then used to determine a tooth color structure of the first and second false color area 21a/21b, 22a/22b as described in FIG. 4.

FIG. 4 illustrates a further step of the invention in which a tooth color structure of the first false color area 21a, 21b and second false color area 22a, 22b are determined. The first false color area 21a and the second false color area 22a correspond to the areas determined in the method step illustrated in FIG. 2, and first false color area 21b and the second false color area 22b correspond to the areas determined in the method step illustrated in FIG. 3. The tooth color structure may be provided in the form of data comprising data about the size and position of the areas 21a, 21b, 22a, 22b in the image. Further the tooth color structure maybe provided in the form of a tooth structure code representative of that tooth color structure.

The relevant tooth 10 may be identified, and the image may be restricted to a portion representing only the tooth 10. In other words the outline of the tooth 10 may be determined and the image may be cropped to the area within the outline. The shape of the tooth and thus the outline may be determined manually by a user, for example by drawing a spline in the image. The skilled person will recognize the possibility of automatic cropping eventually in combination with manual correction. The restriction of the image to a particular tooth may be performed prior to posterization or after.

Figure 5:
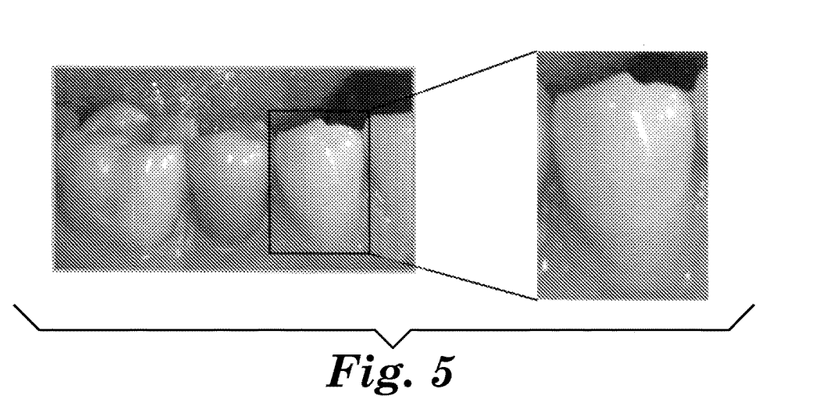
FIG. 5 illustrates a step of determining a tooth color according to an embodiment of the invention.

FIG. 5 illustrates a further step of the invention in which the overall color of the tooth to be restored (or a neighboring tooth) is determined. It is noted that the determination of the tooth color structure as described above and the determination of the overall color as described in the following do not need to be performed in the order described. In contrast, the determination of the overall color may be performed prior to or during the determination of the tooth color structure.

In the example shown the overall color of the tooth 10 is determined from the image data of the image captured from the tooth. Thereby the different colors in the overall area of the tooth 10 are averaged and provided in the form of a tooth color code. The skilled person is however aware of other methods for color measuring, for example by measuring the color using a color measuring device as for example available under the designation Easyshade from the company VITA Zahnfabrik H. Rauter GmbH & Co. KG, Germany.

Figure 6:
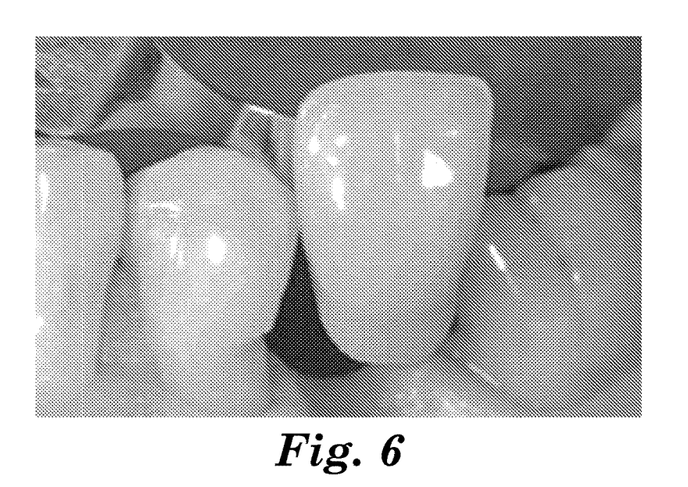
FIG. 6 illustrates a step of determining a tooth color according to a further embodiment of the invention.

FIG. 6 illustrates a further step in which the overall color of the tooth to be restored (or a neighboring tooth) is determined using a shade guide, for example as available from the company VITA Zahnfabrik H. Rauter GmbH & Co. KG, Germany.

Figure 7:
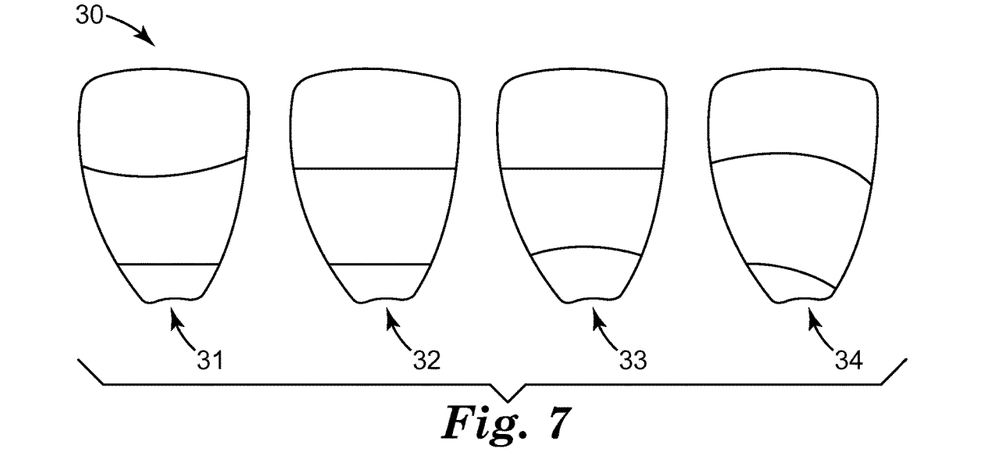
FIG. 7 is a schematic view of a shade guide as it may be used with the present invention.

FIG. 7 shows a shade guide 30 comprising a plurality of shade specimens 31, 32, 33, 34. The shade guide 30 comprises a plurality of specimens defining two or more color areas. The specimens 31-34 differ in the proportioning in which individual color areas are arranged. The color areas in the example are identified by borderlines. Thus different color structures are provided on the different specimens 31-34, which can be matched with a tooth color structure of a patient's tooth. The actual color of the specimens 31-34 is independent from the color structure and may be different from the color of natural teeth. In the example the specimens 31-34 are colorless (for example transparent or pure white) with black borderlines. Accordingly the actual color of the specimens 31-34 preferably does not influence the matching of the color structure. The skilled person will recognize that other colors for the specimens and the borderlines may be used as appropriate.

In the example the shade guide 30 exhibits a coding providing the tooth structure code. Such a shade guide may be used, for example, to determine the tooth color structure of that tooth.

Figure 8:
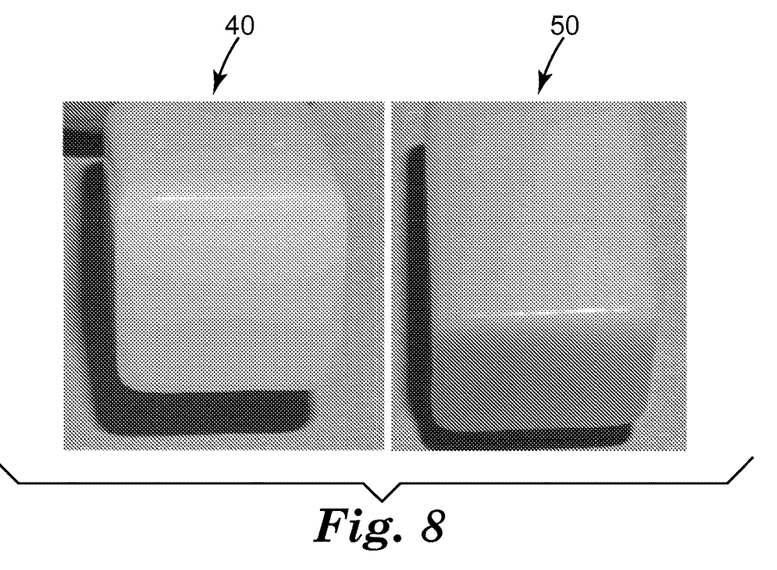
FIG. 8 is a perspective view of blocks as they may be used in the method of the invention.

FIG. 8 illustrates a kit of differently colored blocks 40, 50. Each of the blocks 40, 50 is multicolored. In particular each of the blocks has a predetermined color shading which is preferably non-uniform in at least one dimension of the respective block 40, 50. For example each block 40, 50 may in one dimension be made of two or more zones, with the zones having different colors. Each zone further exhibits a certain translucency so that different zones may have different translucencies. It is noted that a block may be made of a precursor of the final material. For example the block may be made of a pre-sintered ceramic or glass-ceramic material. In such a case the different colors and/or different translucencies as disclosed herein refer to the colors and/or translucencies at the material's final stage, for example after sintering.

In the example the blocks 40, 50 are made of a dental material. Suitable dental materials comprise ceramic, glass-ceramic and dental composite materials.

According to the invention information about the multi-colored milling block are provided, for example in the form of a block color code which is representative of an overall color of the block. Further such information may comprise data about the block color structure, in particular about dimensions and positions of the different block color zones relative to each other and relative to outer boundaries of the block.

In one step a block 40/50 is selected based on the block color code and the tooth color code. In a further step the tooth color structure is matched with the block color structure as illustrated in FIG. 9.

Figure 9:
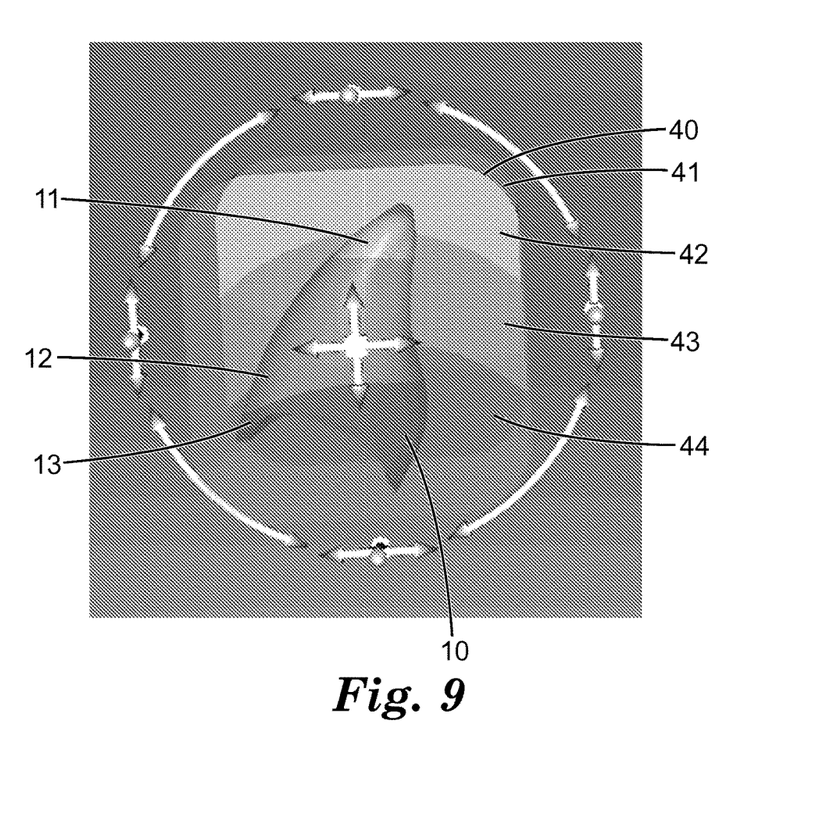
FIG. 9 illustrates steps of determining a position of the tooth color structure in the blank according to an embodiment of the invention.

FIG. 9 shows a virtual representation of a block 40 as an image. The block 40 has four block color zones 41, 42, 43 and 44. In the example the four color zones 41, 42, 43, 44 are formed by curved layers which extend through the block 40 at relatively uniform cross-section. Thus the layers are arranged in only one dimension of the block but provide variations in color in two dimensions due to the curved configuration of the layer cross-sections. The skilled person will recognize that the zones may be provided at any desired shape. However for minimizing the complexity, for example during matching, a relatively simple and geometrically defined shape of the individual zones is advantageous. Further it has been found that a structure as illustrated is sufficient for a multiplicity of different situations.

Further an image of the tooth 10 is overlaid with the image of a block 40. The images in the example are displayed as two- or preferably three-dimensional renderings to a user, so that the user can move and/or rotate the image of the tooth 10 relative to the image of the block 40. As illustrated the image of the tooth 10 has a tooth color structure comprising color areas 11, 12, 13. In the example the tooth color areas 11, 12, 13 have a color which resembles the color of the block color zones 42, 43, 44 respectively. Although the dimensions and positions of the tooth color areas 11, 12, 13 do not exactly match with the dimensions and positions of the block color zones 42, 43, 44, the user can move and/or rotate the image of the tooth 10 and the image of the block 40 relative to each other to provide a relatively good match. Although the skilled person is aware of automatic matching algorithms (with or without any display to a user) it may be advantageous to perform the matching manually, in cases in which a user desires personal influence on the optical appearance of the dental restoration.

Once the position and orientation of the image of the tooth 10 and the image of the block 40 relative to each other is determined through matching, the dental restoration can be machined from the block 40 at the determined position and orientation. Each of the image of the tooth 10 and the image of the block 40 preferably are represented in a coordinate system, for example a Cartesian three-dimensional coordinate system. By determining the difference of the origins and the difference of the angulations between these coordinate systems in all dimensions, the position and orientation of the image of the tooth 10 and the image of the block 40 relative to each other can be determined.

The invention claimed is:

1. A method of making a dental restoration, comprising the steps of:
   capturing an image of a tooth at a color depth that is based on a multiplicity of color values;
   posterizing the image by:
   detecting in the tooth image a contiguous first tooth color area having color values within a predetermined first range of different color values and assigning the first tooth color area one common first false color value; and
   detecting in the tooth image a contiguous second tooth color area having color values within a predetermined second range of different color values and assigning the second tooth color area one common second false color value;
   determining a tooth color structure based on the first and second false color value of the first and second color area, respectively, within the tooth image;
   providing information about a multicolored block that has a predetermined color shading formed by at least a first block color zone and a second block color zone, wherein the information comprises data about a block color structure with respect to dimensions and/or positions of the first and second block color zone;
   matching the tooth color structure and the block color structure; and based on the matching;
   determining a position within the multicolored block in which the tooth color structure and the block color structure match within predetermined limits; and
   machining the dental restoration from the multicolored block at the determined position.

2. The method of claim 1, wherein the step of capturing the tooth image further comprises taking a two-dimensional photograph from the tooth.

3. The method of claim 2, wherein the step of capturing the tooth image further comprises determining an outline of the tooth based on the two-dimensional photograph and thereby creating the tooth image.

4. The method of claim 1, wherein the step of posterization is based on thresholding.

5. The method of claim 1, wherein the first false color value and the second false color value each correspond to a value in a grey scale or correspond to black and white, respectively.

6. The method of claim 1, further comprising the steps of:
   providing a database holding information about a plurality of blocks with each of the blocks having a shade structure in accordance with the first block color zone and the second block color zone, wherein each block being assigned an overall block color code which is based on the colors of the first block color zone and the second block color zone in combination;
   determining a tooth color code; and
   selecting a block having a block color code corresponding to the tooth color code.

7. The method of claim 6, further comprising the step of:
   determining an average color value from the tooth image and calculating the tooth color code.

8. The method of claim 6, further comprising the step of:
   determining the tooth color code by matching a physical shade guide and the tooth.

9. The method of claim 1, further comprising the steps of:
   displaying at least part of the tooth image and the tooth color structure; and
   modifying boundaries of the tooth color structure based on user input.

10. The method of claim 1, further comprising the steps of:
    providing a three-dimensional virtual model of the dental restoration; and
    creating a positional relationship between the tooth color structure and the dental restoration model; and
    wherein the step of machining the dental restoration is controlled based on the dental restoration model.

11. The method of claim 10, further comprising the steps of:
    scanning a patient's teeth;
    designing the dental restoration based on the scan and thereby provide the dental restoration model; and
    transferring the dental restoration model by data transfer to a machine for machining the dental restoration.

12. The method of claim 1, wherein the block is made of a ceramic or glass ceramic material.

13. The method of claim 1, wherein the step of machining the dental restoration involves milling and/or grinding.

14. The method of claim 13, wherein the dental restoration is machined at a position in which the tooth color structure and the block color structure match, wherein the position is determined based on the tooth color code.

* * * * *